United States Patent [19]

McGarrity et al.

[11] Patent Number: 5,451,684
[45] Date of Patent: Sep. 19, 1995

[54] ASYMMETRIC HYDROGENATION OF FUROIMIDAZOLE DERIVATIVES

[75] Inventors: John McGarrity, Visp; Felix Spindler, Starrkirch-Wil; Rudolf Fuchs, Sion; Martin Eyer, Brig-Glis, all of Switzerland

[73] Assignee: Lonza Ltd., Gampel/Valais, Switzerland

[21] Appl. No.: 239,588

[22] Filed: May 9, 1994

[30] Foreign Application Priority Data

May 14, 1993 [CH] Switzerland ............ 1452/93

[51] Int. Cl.$^6$ ........................................ C07D 491/048
[52] U.S. Cl. .................................. 548/303.1
[58] Field of Search ...................... 548/303.1

[56] References Cited

U.S. PATENT DOCUMENTS

| | | | |
|---|---|---|---|
| 3,849,480 | 11/1974 | Knowles et al. | 260/490 |
| 4,409,397 | 10/1983 | Paxson | 562/496 |
| 4,851,540 | 7/1989 | McGarrity et al. | 548/110 |
| 5,171,892 | 12/1992 | Burk | 568/12 |
| 5,187,136 | 2/1993 | Klobucar et al. | 502/162 |

FOREIGN PATENT DOCUMENTS

| | | |
|---|---|---|
| 0270076 | 6/1988 | European Pat. Off. |
| 0273270 | 7/1988 | European Pat. Off. |
| 2058248 | 6/1971 | Germany |

OTHER PUBLICATIONS

Cotton et al. Anorganische Chemie, 3rd Ed. (1974) p. 776 (5).
Morimoto, Toshiaki; Chiba, Mitsuo and Achiwa, Kazuo Tetrahedron Letters, vol. 29, No. 37, pp. 4755–4758, 1988.
Houben-Weyl, Methoden der org. Chem., vol. 15, Thieme Verlag, Stuttgart, (1974).
Patricia A. MacNeil, et al., J. Am. Chem. Soc., (1981), 103, 2273.
K. Achiwa, J. Am. Chem., Soc., (1976), 98, p. 8265, Dec.
G. Giordano et al., Inorg. Synth., (1979), 19, p. 218.
J. Chatt et al., J. Chem. Soc., (1957), 4735.

*Primary Examiner*—Robert W. Ramsuer
*Assistant Examiner*—Laura L. Stockton
*Attorney, Agent, or Firm*—Fisher, Christen & Sabol

[57] ABSTRACT

A process for the asymmetric hydrogenation of furoimidazole derivatives of the general formula:

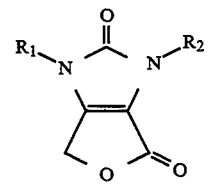

I wherein $R_1$ is a protective group and $R_2$ is hydrogen or a protective group, with hydrogen in the presence of a homogeneous catalyst to give the corresponding diastereomeric dihydrofuroimidazole derivatives of the general formula:

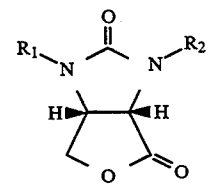

II

The dihydrofuroimidazole derivatives of the general formula II are intermediates for the preparation of the vitamin (+)-biotin.

18 Claims, No Drawings

ASYMMETRIC HYDROGENATION OF FUROIMIDAZOLE DERIVATIVES

BACKGROUND OF THE INVENTION
1. Field of the Invention

The invention relates to a process for the asymmetric hydrogenation of furoimidazole derivatives of the general formula:

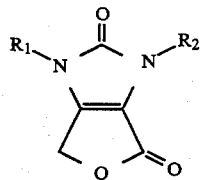

I in which $R_1$ denotes a protective group which can be eliminated in a known manner, and $R_2$ represents hydrogen or a protective group which can be eliminated in a known manner, with hydrogen in the presence of a homogeneous catalyst to give the corresponding diastereomeric dihydrofuroimidazole derivatives of the general formula:

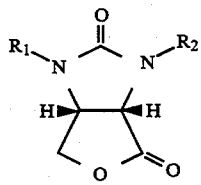

II in which $R_1$ and $R_2$ have the above-stated meaning.

2. Background Art

Most of the known (+)-biotin syntheses pursue the aim of separating suitable precursors by racemate resolution methods, some of which are very elaborate and some of which use very costly resolving agents, and continuing the (+)-biotin synthesis with the resultant enantiomers (compare, for example, German Patent No. 2,058,248). According to European Patent No. 273,270, introduction of the correct configuration, that is to say (S) in the 3a and (R) in the 6a position of the biotin ring structure, was then achieved for the first time by asymmetric hydrogenation of corresponding furoimidazole derivatives with a classical hydrogenation catalyst, such as, rhodium on aluminium oxide. However, this process was unable to provide complete satisfaction in terms of the yield of desired diastereomer which was achievable.

BROAD DESCRIPTION OF THE INVENTION

The object of the invention is to provide an improved asymmetric hydrogenation process with which the key step in biotin synthesis can be carried out with a very good diastereoselectivity and good yield of the dihydropyrimidazole. Other objects and advantages of the invention are set out herein or obvious herefrom to one skilled in the art.

The objects and advantages of the invention are achieved by the process of the invention.

The invention involves a process for the asymmetric hydrogenation of furoimidazole derivatives of the general formula:

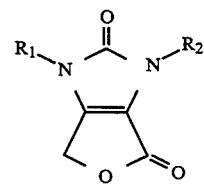

I in which $R_1$ denotes a protective group which can be eliminated in a known manner, and $R_2$ represents hydrogen or a protective group which can be eliminated in a known manner, with hydrogen in the presence of a homogeneous catalyst to give the corresponding diastereomeric dihydrofuroimidazole derivatives of the general formula:

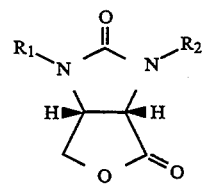

II in which $R_1$ and $R_2$ have the above-stated meaning. The homogeneous catalysts, which are formed from a Rh complex and a chiral phosphine ligand selected from one of the following general formulas V to VIII:

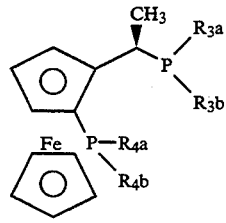

V in which $R_{3a}$ and $R_{3b}$ are identical or different and denote $C_1$–$C_{12}$-alkyl, $C_5$–$C_7$-cycloalkyl or $C_6$–$C_{12}$-aryl, and $R_{4a}$ and $R_{4b}$ have the meaning indicated for $R_{3a}$ and $R_{3b}$,

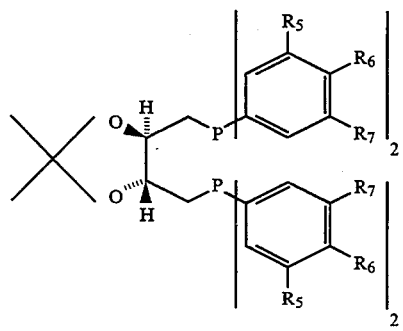

VI in which $R_5$ and $R_7$ have the meaning indicated above for $R_{3a}$ and $R_{3b}$, and $R_6$ denotes $C_1$–$C_4$-alkoxy or $C_1$–$C_4$-dialkylamino:

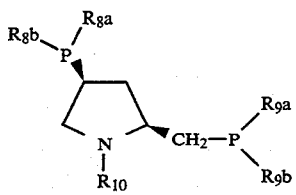

VII in which $R_{8a}$, $R_{8b}$, $R_{9a}$, $R_{9b}$ have the above-meaning indicated for $R_{3a}$ and $R_{3b}$, and $R_{10}$ denotes hydrogen or an $NH_2$ protective group, and

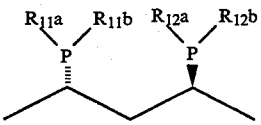

VIII in which $R_{11a}$, $R_{11b}$ and $R_{12a}$, $R_{12b}$ have the above-meaning indicated for $R_{3a}$ and $R_{3b}$, are employed.

Preferably the protective group which can be eliminated in a known manner and is employed for $R_1$, is a 1-phenyl-($C_1$–$C_6$)-alkyl group or a 1-naphthyl-($C_1$–$C_6$)-alkyl group, where the aromatic nuclei of the particular groups are optionally substituted by one or more substituents from the series comprising ($C_1$–$C_6$)-alkyl, ($C_1$–$C_6$)-alkoxy, hydroxyl, halo, amino, ($C_1$–$C_6$)-alkylamino or ($C_1$–$C_6$)-dialkylamino. Preferably the protective group, which can be eliminated in a known manner for $R_2$, is a ($C_1$–$C_6$)-alkanoyl group, a ($C_1$–$C_6$)-alkoxy-($C_1$–$C_6$)-alkyl group, a ($C_1$–$C_6$)-alkoxycarbonyl group, an aroyl group or a benzyl group, where the aromatic nuclei of the particular groups are optionally substituted by one or more substituents from the series comprising ($C_1$–$C_6$)-alkyl, ($C_1$–$C_6$)-alkoxy, hydroxyl, halo, amino, ($C_1$–$C_6$)-alkylamino and ($C_1$–$C_6$)-dialkylamino.

Preferably a chiral phosphine ligand selected from the compounds of the general formula V or VI is used. Preferably the chiral phosphine ligand employed is (R)-(S)-PPF-Pcy2 (general formula V with $R_{3a}$, $R_{3b}$ being cyclohexyl and $R_{4a}$, $R_{4b}$ being phenyl), (R)-(S)-PPF-PtBu2 (general formula V with $R_{3a}$, $R_{3b}$ being t-butyl and $R_{4a}$, $R_{4b}$ being phenyl), or (4R, 5R)-MOD-DIOP (general formula VI with $R_5$, $R_7$ being methyl and $R_6$ being methoxy). Preferably a Rh complex of the general formula:

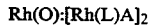   III or

   IV in which L represents two $C_2$–$C_{12}$ olefins or one $C_5$–$C_{12}$-diene; A represents a halogen and B represents an anion of an oxo acid or of a complex acid, is employed.

Preferably the reaction is carried out under a hydrogen pressure of 1 to 200 bar and at a reaction temperature of 25° to 150° C. Preferably the amount of the homogeneous catalyst, expressed as molar ratio of the furoimidazole derivative to the homogeneous catalyst, is in the range 100:1 to 10,000:1. Preferably an aprotic solvent is employed. Preferably toluene is employed as the aprotic solvent.

The dihydrofuroimidazoles of the general formula II are important intermediates in the synthesis of (+)-biotin, which is a vitamin essential for humans and is also called vitamin H. (+)-Biotin is additionally employed as pharmaceutical for the treatment of dermatoses or as feed additive with growth-promoting action for useful livestock.

BRIEF DESCRIPTION OF THE INVENTION

The furoimidazoles of the general formula I can be prepared by the methods of European Patent No. 273,270 or European Patent No. 270,076.

It is expedient to employ the following groups as protective groups which can be eliminated in a known manner for $R_1$: $R_1$ can be a 1-phenyl-($C_1$–$C_6$)-alkyl group or a 1-naphthyl-($C_1$–$C_6$)-alkyl group. The aromatic nuclei thereof can, where appropriate, be substituted by one or more substituents from the series comprising ($C_1$–$C_6$)-alkyl, ($C_1$–$C_6$)-alkoxy, hydroxyl, halo, amino, ($C_1$–$C_6$)-alkylamino, and ($C_1$–$C_6$)-dialkylamino. The 1-phenyl-($C_1$–$C_6$)-alkyl group or the 1-naphthyl-($C_1$–$C_6$)-alkyl group can have a chiral center. $R_1$ preferably is an (R)- or (S)-1-phenylethyl group, a benzyl group or an (R)- or (S)-1-naphthylethyl group; the aromatic nuclei of the preferred groups can be substituted by the specified substituents. $R_2$ can represent hydrogen or represent protective groups which can be eliminated in a known manner and are from the series comprising ($C_1$–$C_6$)-alkanoyl, benzyl, ($C_1$–$C_6$)-alkoxy-($C_1$–$C_6$)-alkyl, ($C_1$–$C_6$)-alkoxycarbonyl and aroyl, such as, benzoyl. The aromatic nucleus of the benzyl group or the aroyl groups can be substituted as for the aromatic nuclei of $R_1$. $R_2$ preferably has the meaning of hydrogen, acetyl, benzyl, ($C_1$–$C_2$)-alkoxy-($C_1$–$C_2$)-alkyl, ($C_1$–$C_2$)-alkoxycarbonyl or benzoyl.

It has been found, surprisingly, that homogeneous catalysts formed from a Rh complex and a chiral phosphine ligand show a high stereoselectivity with, as a rule, a good yield.

The Rh complexes used are those of the general formula:

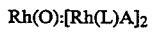   III or

   IV in which L represents two $C_2$–$C_{12}$ olefins or one $C_5$–$C_{12}$ diene; A denotes a halogen and B denotes an anion of an oxo acid or complex acid. L in the meaning of olefin preferably contains 2 to 6 C atoms and in the meaning of diene preferably contains 5 to 8 C atoms. The diene can moreover be open-chain, mono- or bicyclic. Examples of olefins are: ethylene, propene and 1-butene. Examples of dienes are: 1,5-hexadiene, 1,4-cyclohexadiene, 1,4- or 1,5-heptadiene, 1,4-cycloheptadiene, 1,4- or 1,5-octadiene, 1,4- or 1,5-cyclooctadiene, and norbornadiene. L preferably represents two ethylene or one 1,5-hexadiene, 1,5-cyclooctadiene or norbornadiene.

A preferably represents chlorine or bromine. Examples of B are: $ClO_4^-$, $FSO_3^-$, $CH_3SO_3^-$, $CF_3SO_3^-$, $BF_4^-$, $PF_6^-$, $SbCl_6^-$, $AsF_6^-$ and $SbF_6^-$. B preferably denotes: $BF_4^-$, $ClO_4^-$, $PF_6^-$, $CF_3SO_3^-$ and $SbF_6^-$.

The preparation of these Rh complexes is known and is disclosed, for example, in J. Chatt et al., J. Chem.

Soc., (1957), 4735, or G. Giordano et al., Inorg. Synth., (1979), 19, 218.

The following compounds are used as chiral phosphine ligands:

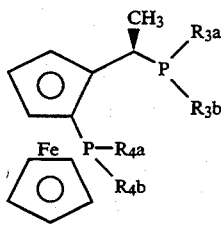

V $R_{3a}$ and $R_{3b}$ are identical or different and denote $C_1$-$C_{12}$-alkyl, $C_5$-$C_7$-cycloalkyl or $C_6$-$C_{12}$-aryl, and $R_{4a}$ and $R_{4b}$ are identical or different and denote $C_1$-$C_{12}$-alkyl, $C_5$-$C_7$-cycloalkyl or $C_6$-$C_{12}$-aryl. $R_{3a}$ and $R_{3b}$ are preferably identical. $R_{3a}$ and $R_{3b}$ in the meaning of alkyl can be linear or branched and preferably contain 1 to 6, particularly preferably 1 to 4, C atoms. Preferably alkyl groups are methyl, ethyl, propyl, i-propyl, and n-, i- and t-butyl, particularly preferably i-propyl or t-butyl. $R_{3a}$ and $R_{3b}$ in the meaning of cycloalkyl preferably have the meaning of cyclohexyl. $R_{3a}$ and $R_{3b}$ in the meaning of aryl can denote optionally substituted phenyl or naphthyl. Suitable substituents are alkyl groups or alkoxy groups with 1 to 4 C atoms or a $C_1$-$C_4$-dialkylamino group. $R_{4a}$ and $R_{4b}$ can have the meanings specified for $R_{3a}$ and $R_{3b}$. $R_{4a}$ and $R_{4b}$ particularly preferably represents a phenyl group.

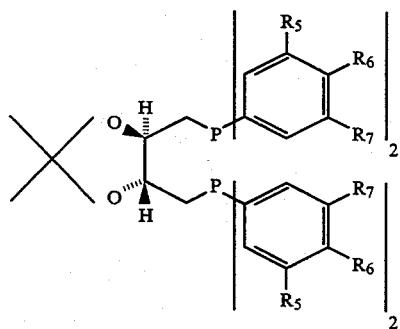

VI $R_5$ and $R_7$ are identical or different and denote $C_1$-$C_4$-alkyl, $R_6$ denotes $C_1$-$C_4$-alkoxy or $C_1$-$C_4$-dialkylamino. $R_5$ and $R_7$ preferably have the same meaning. $R_5$ and $R_7$ in the meaning of alkyl can be linear or branched. The preferred alkyl group is the methyl group. $R_6$ preferably has the meaning of methoxy or dimethylamino. The phosphine ligands of the general formula VI are known from the literature [T. Morimoto et al., Tetrahedron Letters, (1988), 29, 4755].

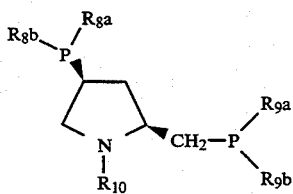

VII $R_{8a}$ and $R_{8b}$ expediently have the meaning specified for $R_{3a}$ and $R_{3b}$. The preferred meaning of $R_{8a}$ and $R_{8b}$ is cyclohexyl or phenyl. $R_{9a}$ and $R_{9b}$ expediently have the meaning indicated for $R_{3a}$ and $R_{3b}$. The preferred meaning is phenyl. $R_{10}$ expediently has of hydrogen or a conventional $NH_2$ protective group. By a conventional $NH_2$ protective group is meant those described in Houben-Weyl, Methoden der org. Chem., Vol. 15, Thieme Verlag, Stuttgart, (1974). Examples are the t-butoxycarbonyl or the benzyloxycarbonyl group. The compounds of the general formula VII are known from the literature [K. Achiwa, J. Am. Chem. Soc., (1976), 98, 8265].

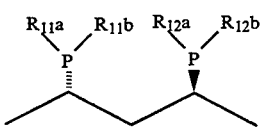

VIII $R_{11a}$, $R_{11b}$ and $R_{12a}$, $R_{12b}$ expediently have the meaning specified for $R_{3a}$ and $R_{3b}$, $R_{11a}$, $R_{11b}$ and $R_{12a}$, $R_{12b}$ preferably represents phenyl. The compounds of the general formula VIII are known from the literature [Patricia A. MacNeil et al., J. Am. Chem. Soc., (1981), 103, 2273].

The active homogeneous catalyst is expediently formed in situ, that is to say, during the hydrogenation of the relevant furoimidazole of the general formula I. However, it is equally possible first to isolate from the phosphine ligand and the Rh complex a so-called catalyst precursor which can be added to the reaction separately.

However, the expedient procedure is such that first the homogeneous catalyst components, that is to say the Rh complex and the appropriate phosphine ligand, are introduced together with the appropriate furoimidazole derivative into a suitable inert solvent.

Suitable and expedient solvents, which can be used alone or in a mixture, are aprotic solvents, such as, aliphatic or aromatic hydrocarbons or halogenated hydrocarbons. Suitable representatives of the aromatic hydrocarbons are, for example, benzene, toluene or xylene, the aliphatic hydrocarbons are, for example, hexane or pentane, and the halogenated hydrocarbons are methylene choride or chloroform. A particularly suitable solvent is toluene. It may in some circumstances be advantageous to use a mixture of the specified solvents with a protic solvent, Such as, with aliphatic alcohols. A particularly suitable aliphatic alcohol is methanol.

The amount of solvent is expediently chosen so that a substrate concentration of 2 to 20 percent results. A substrate concentration of about 10 percent is preferably used.

The amount of catalyst, expressed as a ratio of substrate (furoimidazole) to catalyst, is expediently in the range between 100:1 and 10,000:1, preferably in the range between 500:1 and 2,000:1.

The reaction is advantageously carried out under a hydrogen pressure of between 1 bar and 200 bar, preferably 10 bar to 100 bar, and at a reaction temperature between 25° and 150° C., preferably 40° and 90° C.

After the hydrogenation, which usually lasts 2 to 6 hours, the desired stereoisomeric (3aS, 6aR)-dihydrofuroimidazole of the general formula II can be isolated in a prior art manner.

Any amount of the undesired (3aR, 6aS)-dihydrofuroimidazole which is present can be removed by recrystallization using a suitable solvent, such as, methyl isobutyl ketone, ethyl acetate and toluene.

The resultant dihydrofuroimidazoles can then be reacted further, for example, as described in European Patent No. 273,270, to give (+)-biotin.

EXAMPLES

The hydrogenation examples which are listed in tabular form were carried out in analogy to the following method:

0.01 mol of the appropriate furoimidazole derivative (Table 1) was introduced into a 50 ml steel autoclave. 0.001 mmol of Rh complex (Table 2) and 0.002 mmol of the appropriate phosphine ligand (Table 3) were successively dissolved in 25 ml of solvent in a 10 ml Schlenk vessel and then stirred at room temperature for 30 minutes. This catalsyt solution was transferred by means of a steel capillary into the autoclave which was under an argon atmosphere, and subsequently the autoclave was heated to the temperature T over 45 minutes. After flushing with $H_2$, the $H_2$ pressure p was injected. The reaction was stopped after the reaction time t. The conversion and the stereoselectivity (diastereoselectivity/enanthioselectivity) of the resulting dihydrofuroimidazoles were determined by 1H-NMR (400 MHz) or by HPLC.

TABLE 1

| | Furoimidazole derivatives employed: | |
|---|---|---|
| | $R_1$ | $R_2$ |
| A | (R)-1-Phenylethyl | H |
| B | Benzyl | H |
| C | (R)-1-Phenylethyl | Benzyl |
| D | (R)-1-(2-Methoxyphenyl)ethyl | H |
| E | 2-Methoxybenzyl | H |
| F | (R)-1-(1-Naphthyl)ethyl | H |
| G | (R)-1-Phenylethyl | Acetyl |

TABLE 2

| Rh complexes employed: | |
|---|---|
| Rh(O) | [Rh(norbornadiene)Cl]$_2$ |
| Rh(I) | [Rh (norbornadiene)$_2$]BF$_4$ |

TABLE 3

| | Chiral phosphine ligands employed: | |
|---|---|---|
| General formula | Definition of the radicals | Short name |
| V(a) | $R_{3a}, R_{3b}$ = Cyclohexyl<br>$R_{4a}, R_{4b}$ = Phenyl | (R)-(S)-PPF-Pcy2 |
| V(b) | $R_{3a}, R_{3b}$ = t-Butyl<br>$R_{4a}, R_{4b}$ = Phenyl | (R)-(S)-PPF-PtBu2 |
| VI | $R_5, R_7$ = Methyl<br>$R_6$ = Methoxy | (4R,5R)-MOD-DIOP |
| VII(a) | $R_{8a}, R_{8b}$ = Cyclohexyl<br>$R_{9a}, R_{9b}$ = Phenyl<br>$R_{10}$ = t-Butoxycarbonyl | (2S,4S)-BCPM |
| VII(b) | $R_{8a}, R_{8b}$ = Phenyl<br>$R_{9a}, R_{9b}$ = Phenyl<br>$R_{10}$ = t-Butoxycarbonyl | (2S,4S)-BPPM |
| VIII | $R_{11a}, R_{11b}$ = Phenyl<br>$R_{12a}, R_{12b}$ = Phenyl | (2S,4S)-BDPP |

TABLE 4

Examples carried out:

| Examples | Furoimidazole (Table 1) | Rh Complex (Table 2) | Ligand (Table 3) | Solvent | Pressure p (bar) | Temperature T(°C.) | Reaction time t (h) | Conversion [%] | D ratio or E ratio# [%] |
|---|---|---|---|---|---|---|---|---|---|
| 1 | A | Rh(0) | VIIb | CH$_2$Cl$_2$ | 35 | 25 | 48 | 29 | 72:28 |
| 2 | A | Rh(0) | V(a) | Tol/MeOH 25/3 | 30 | 70 | 28 | 95 | 90:10 |
| 3 | A | Rh(0) | VI | Toluene | 35 | 70 | 3 | 100 | 85:15 |
| 4 | A | Rh(I) | VI | Tol/MeOH 1/1 | 70 | 60 | 19 | 73 | 80:20 |
| 5 | A | Rh(I) | VII(A) | THF | 70 | 60 | 43 | 49 | 34:66 |
| 6 | A | Rh(0) | V(b) | Toluene | 50 | 70 | 18 | 100 | 99:1 |
| 7 | A | Rh(0) | VIII | Tol/MeOH 4/1 | 35 | 70 | 19 | 51 | 75:25 |
| 8 | C | Rh(0) | VI | Toluene | 30 | 70 | 67 | 9 | 60:40 |
| 9 | D | Rh(0) | VI | Toluene | 30 | 70 | 16 | 12 | 92:8 |
| 10 | D | Rh(0) | V(b) | Toluene | 50 | 70 | 19 | 72 | 99:1 |
| 11 | B | Rh(0) | VI | Toluene | 35 | 70 | 3 | 95 | 95:5# |
| 12 | B | Rh(0) | V(b) | Toluene | 50 | 70 | 18 | 95 | 95:5# |
| 13 | E | Rh(0) | V(b) | Toluene | 50 | 70 | 18 | 95 | 90:10# |
| 14 | F | Rh(0) | VI | Toluene | 30 | 70 | 20 | 97 | 99:1 |
| 15 | G | Rh(0) | V(b) | Toluene | 50 | 70 | 69 | 99 | 57:43 |

What is claimed is:

1. A process for the asymmetric hydrogenation of a furoimidazole derivative of formula:

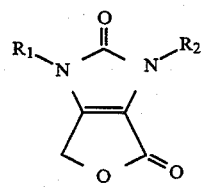

I wherein $R_1$ is a protective group which can be eliminated in a known manner, and $R_2$ is hydrogen or a protective group which can be eliminated in a known manner, with hydrogen in the presence of a homogeneous catalyst to give the corresponding diastereomeric dihydrofuroimidazole derivative of formula:

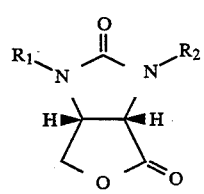

II wherein $R_1$ and $R_2$ have the above-stated meaning, characterized in that a homogeneous catalyst, which is formed from a Rh complex and a chiral phoshine ligand selected from one of formulae V to VIII:

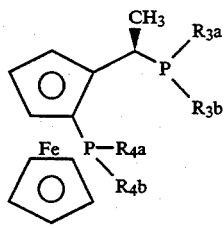   V wherein $R_{3a}$ and $R_{3b}$ are identical or different and each is $C_1$–$C_{12}$-alkyl, $C_5$–$C_7$-cycloalkyl or $C_6$–$C_{12}$-aryl, and $R_{4a}$ and $R_{4b}$ have the meaning indicated above for $R_{3a}$ and $R_{3b}$,

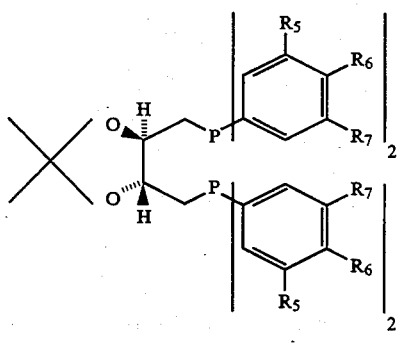   VI wherein $R_5$ and $R_7$ have the meaning indicated above for $R_{3a}$ and $R_{3b}$, and $R_6$ is $C_1$–$C_4$-alkoxy or $C_1$–$C_4$-dialkylamino,

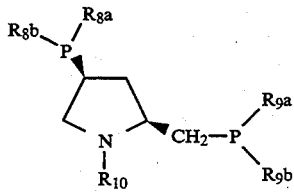   VII wherein $R_{8a}$, $R_{8b}$ and $R_{9a}$, $R_{9b}$ have the meaning indicated above for $R_{3a}$ and $R_{3b}$, and $R_{10}$ is hydrogen or an $NH_2$ protective group, and

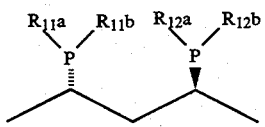   VIII wherein $R_{11a}$, $R_{11b}$, $R_{12a}$ and $R_{12b}$ have the meaning indicated above for $R_{3a}$ and $R_{3b}$, are employed.

2. The process according to claim 1 wherein the protective group, which can be eliminated in a known manner and is employed for $R_1$, is a 1-phenyl-($C_1$–$C_6$)-alkyl group or a 1-naphthyl-($C_1$–$C_6$)-alkyl group, where the aromatic nuclei of the particular groups are optionally substituted by one or more substituents from the group consisting of ($C_1$–$C_6$)-alkyl, ($C_1$–$C_6$)-alkoxy, hydroxyl, halo, amino, ($C_1$–$C_6$)-alkylamino and ($C_1$–$C_6$)-dialkylamino.

3. The process according to claim 2 wherein the protective group which can be eliminated in a known manner for $R_2$ is a ($C_1$–$C_6$)-alkanoyl group, a ($C_1$–$C_6$)-alkoxy-($C_1$–$C_6$)-alkyl group, a ($C_1$–$C_6$)-alkoxycarbonyl group, an aroyl group or a benzyl group, where the aromatic nuclei of the particular groups are optionally substituted by one or more substituents from the group consisting of ($C_1$–$C_6$)-alkyl, ($C_1$–$C_6$)-alkoxy, hydroxyl, halo, amino, ($C_1$–$C_6$)alkylamino and ($C_1$–$C_6$)-dialkylamino.

4. The process according to claim 3 wherein a chiral phosphine ligand selected from the compounds of formula V or VI is used.

5. The process according to claim 4 wherein the chiral phosphine ligand employed is (R)-(S)-PPF-Pcy2, formula V with $R_{3a}$, $R_{3b}$ being cyclohexyl and $R_{4a}$, $R_{4b}$ being phenyl, or (R)-(S)-PPF-PtBu2, formula V with $R_{3a}$, $R_{3b}$ being t-butyl and $R_{4a}$, $R_{4b}$ being phenyl, or (4R, 5R)-MOD-DIOP, formula VI with $R_5$, $R_7$ being methyl and $R_6$ being methoxy.

6. The process according to claim 5 wherein a Rh complex of formula:

$$Rh(O):[Rh(L)A]_2 \qquad \qquad III$$

or $$Rh(I):[Rh(L)_2]_B \qquad \qquad IV$$

wherein L is two $C_2$–$C_{12}$olefins or one $C_{5-C12}$-diene, A is a halogen and B is an anion of an oxo acid or of a complex acid, is employed.

7. The process according to claim 6 wherein the reaction is carried out under a hydrogen pressure of 1 to 200 bar and at a reaction temperature of 25° to 150° C.

8. The process according to claim 7 wherein the amount of the homogeneous catalyst, expressed as molar ratio of the furoimidazole derivative to the homogeneous catalyst, is in the range 100:1 to 10,000:1.

9. The process according to claim 8 wherein an aprotic solvent is employed.

10. The process according to claim 9 wherein toluene is employed as the aprotic solvent.

11. The process according to claim 1 wherein the protective group which can be eliminated in a known manner for $R_2$ is a ($C_1$–$C_6$)-alkanoyl group, a ($C_{l\text{-}C6}$)-alkoxy-($C_1$–$C_6$)-alkyl group, a ($C_1$–$C_6$)-alkoxycarbonyl group, an aroyl group or a benzyl group, where the aromatic nuclei of the particular groups are optionally substituted by one or more substituents from the group consisting of ($C_1$–$C_6$)-alkyl, ($C_1$–$C_6$)-alkoxy, hydroxyl, halo, amino, ($C_1$–$C_6$)alkylamino and ($C_1$–$C_6$)-dialkylamino.

12. The process according to claim 1 wherein a chiral phosphine ligand selected from the compounds of the formula V or VI is used.

13. The process according to claim 1 wherein the chiral phosphine ligand employed is (R)-(S)-PPF-Pcy2, formula V with $R_{3a}$, $R_{3b}$ being cyclohexyl and $R_{4a}$, $R_{4b}$ being phenyl, or (R)-(S) -PPF-PtBu2, formula V with $R_{3a}$, $R_{3b}$ being t-butyl and $R_{4a}$, $R_{4b}$ being phenyl, or (4R, 5R)-MOD-DIOP, formula VI with $R_5$, $R_7$ being methyl and $R_6$ being methoxy.

14. The process according to claim 1 wherein a Rh complex of the general formula:

$$Rh(O):[Rh(L)A]_2 \qquad \qquad III$$

or $$Rh(I):[RH(L)_2]B \qquad IV$$

wherein L is two C$_2$-C$_{12}$ olefins, or one C$_5$-C$_{12}$-diene, A is a halogen and B is an anion of an oxo acid or of a complex acid, is employed.

15. The process according to claim 1 wherein the reaction is carried out under a hydrogen pressure of 1 to 200 bar and at a reaction temperature of 25° to 150° C.

16. The process according to claim 1 wherein the amount of the homogeneous catalsyt, expressed as molar ratio of the furoimidazole derivative to the homogeneous catalsyt, is in the range of 100:1 to 10,000:1.

17. The process according to claim 1 wherein an aprotic solvent is employed.

18. The process according to claim 17 wherein toluene is employed as the aprotic solvent.

* * * * *